(12) United States Patent
Hiraoka et al.

(10) Patent No.: US 11,648,347 B2
(45) Date of Patent: May 16, 2023

(54) MEDICAL DEVICE CONTAINING A CAKE COMPOSITION COMPRISING ARIPIPRAZOLE AS AN ACTIVE INGREDIENT, AND A CAKE COMPOSITION COMPRISING ARIPIPRAZOLE AS AN ACTIVE INGREDIENT

(75) Inventors: Shogo Hiraoka, Osaka (JP); Kiyoshi Taniguchi, Osaka (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 257 days.

(21) Appl. No.: 13/981,229

(22) PCT Filed: Jan. 17, 2012

(86) PCT No.: PCT/JP2012/051285
§ 371 (c)(1),
(2), (4) Date: Jul. 23, 2013

(87) PCT Pub. No.: WO2012/102216
PCT Pub. Date: Aug. 2, 2012

(65) Prior Publication Data
US 2013/0302384 A1    Nov. 14, 2013

(30) Foreign Application Priority Data
Jan. 24, 2011 (JP) .............................. JP2011-011711

(51) Int. Cl.
| A61M 5/19 | (2006.01) |
| A61K 31/496 | (2006.01) |
| A61K 9/19 | (2006.01) |
| B65B 3/00 | (2006.01) |
| A61K 9/00 | (2006.01) |
| A61M 5/28 | (2006.01) |

(52) U.S. Cl.
CPC ................. *A61M 5/19* (2013.01); *A61K 9/19* (2013.01); *A61K 31/496* (2013.01); *B65B 3/00* (2013.01); *A61K 9/0019* (2013.01); *A61M 5/284* (2013.01); *F04C 2270/0421* (2013.01)

(58) Field of Classification Search
CPC ...... A61K 9/0019; A61K 9/19; A61K 31/496; F04C 2270/0421; A61M 5/19; A61M 5/284; B65B 3/00
See application file for complete search history.

(56) References Cited

U.S. PATENT DOCUMENTS

| 5,006,528 A | 4/1991 | Oshiro et al. |
| 5,290,228 A * | 3/1994 | Uemura .................. A61M 5/19 604/220 |
| 5,788,670 A | 8/1998 | Reinhard et al. |
| 5,876,372 A | 3/1999 | Grabenkort et al. |
| 5,971,953 A * | 10/1999 | Bachynsky .................... 604/90 |
| 6,149,628 A | 11/2000 | Szapiro et al. |
| 6,200,627 B1 | 3/2001 | Lubrecht |
| 7,621,887 B2 | 11/2009 | Griffiths et al. |
| 2004/0138611 A1 | 7/2004 | Griffiths et al. |
| 2005/0152981 A1 | 7/2005 | Gleeson et al. |
| 2007/0148100 A1 | 6/2007 | Jenkins |

FOREIGN PATENT DOCUMENTS

| CA | 2 728 116 A1 | 12/2009 |
| EP | 0 511 402 A1 | 11/1992 |
| EP | 0 743 072 A2 | 11/1996 |
| EP | 0 962 229 A2 | 12/1999 |
| EP | 1 036 568 A1 | 9/2000 |
| ES | 2074024 A1 | 8/1995 |
| ES | 2211014 T3 | 7/2004 |
| JP | 58-165852 | 9/1983 |
| JP | 2005-306216 | 11/1993 |
| JP | H05-306216 A | 11/1993 |
| JP | 6-30974 | 2/1994 |
| JP | H0630974 * | 2/1994 |
| JP | 08-112333 | 5/1996 |
| JP | 2005-200409 | 7/2005 |
| JP | 2007-508898 A | 4/2007 |
| JP | 2007-509148 | 4/2007 |
| JP | 2010-025370 | 2/2010 |
| JP | 4536825 B1 | 6/2010 |
| WO | WO 2004/064901 A2 | 8/2004 |
| WO | WO 2005/041937 A2 | 5/2005 |
| WO | WO 2005/058277 | 6/2005 |
| WO | WO 2009/017250 A1 | 2/2009 |

OTHER PUBLICATIONS

International Search Report from the European Patent Office for International Application No. PCT/JP2012/051285, dated May 25, 2012.
Notification of Reasons for Refusal issued by the Japanese Patent Office in Application No. JP 2016-112583, dated Mar. 14, 2017 (5 pages).
Notification of Reasons for Refusal issued by the Japanese Patent Office in Application No. JP 2016-112583, dated Mar. 10, 2017 (5 pages).
Office Action for corresponding JP Application No. 2013-112583 dated Sep. 12, 2017.

(Continued)

*Primary Examiner* — David J Blanchard
*Assistant Examiner* — Thurman Wheeler
(74) *Attorney, Agent, or Firm* — Finnegan, Henderson, Farabow, Garrett & Dunner, LLP

(57) ABSTRACT

The present invention provides a medical device containing a cake composition comprising aripiprazole as an active ingredient and capable of suppressing agglomeration of aripiprazole in a suspension obtained by resuspending a freeze-dried substance; and a cake composition comprising aripiprazole as an active ingredient. The present invention relates to a medical device containing, in a storage container whose inner wall is treated with silicone, a freeze-dried cake composition comprising separately prepared aripiprazole as an active ingredient, wherein there is a space between the inner wall and the cake composition; and a cake composition comprising aripiprazole as an active ingredient and having a strength of 5 to 100 N.

7 Claims, 8 Drawing Sheets

(56) References Cited

OTHER PUBLICATIONS

Office Action dated May 27, 2020 for corresponding AR Patent Application No. P120100209.
Communication of a Notice of Opposition dated Apr. 26, 2022 against the corresponding EP Patent No. 2667856.
Communication of a Notice of Opposition dated May 3, 2022 against the corresponding EP Patent No. 2667856.
Patentee's Appeal Brief to USPTO dated May 7, 2021.
PDA Journal of Pharmaceutical Science and Technology, 1988, vol. 42, No. 6, pp. 199-202.
Pfizer press release "Pfizer Receives FDA Approval for Prefilled Dual-Chamber Syringe for Use in the Treatment of Hemophilia A", dated Aug. 9, 2010.
Third Edition, Informa Healthcare, 2010, chapters 15, 16 and 21.
Third Edition, Informa Healthcare, 2010, chapter 21.

* cited by examiner

[Fig. 1]
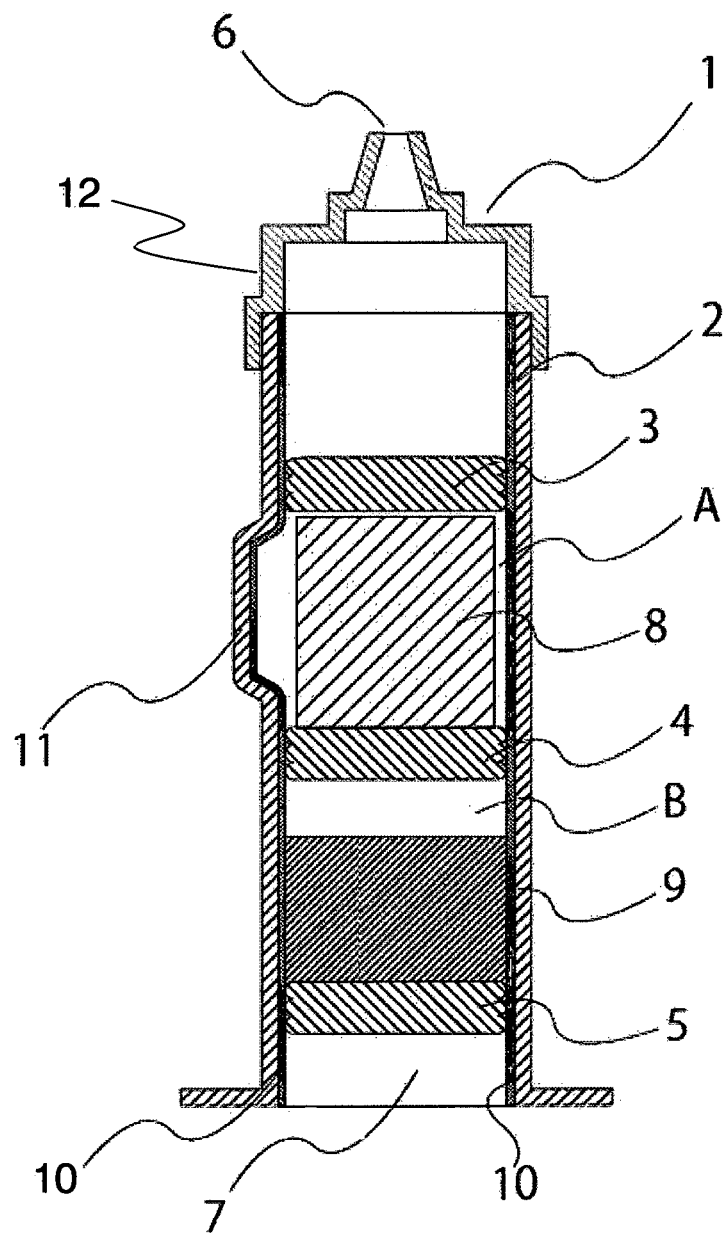

[Fig. 2]
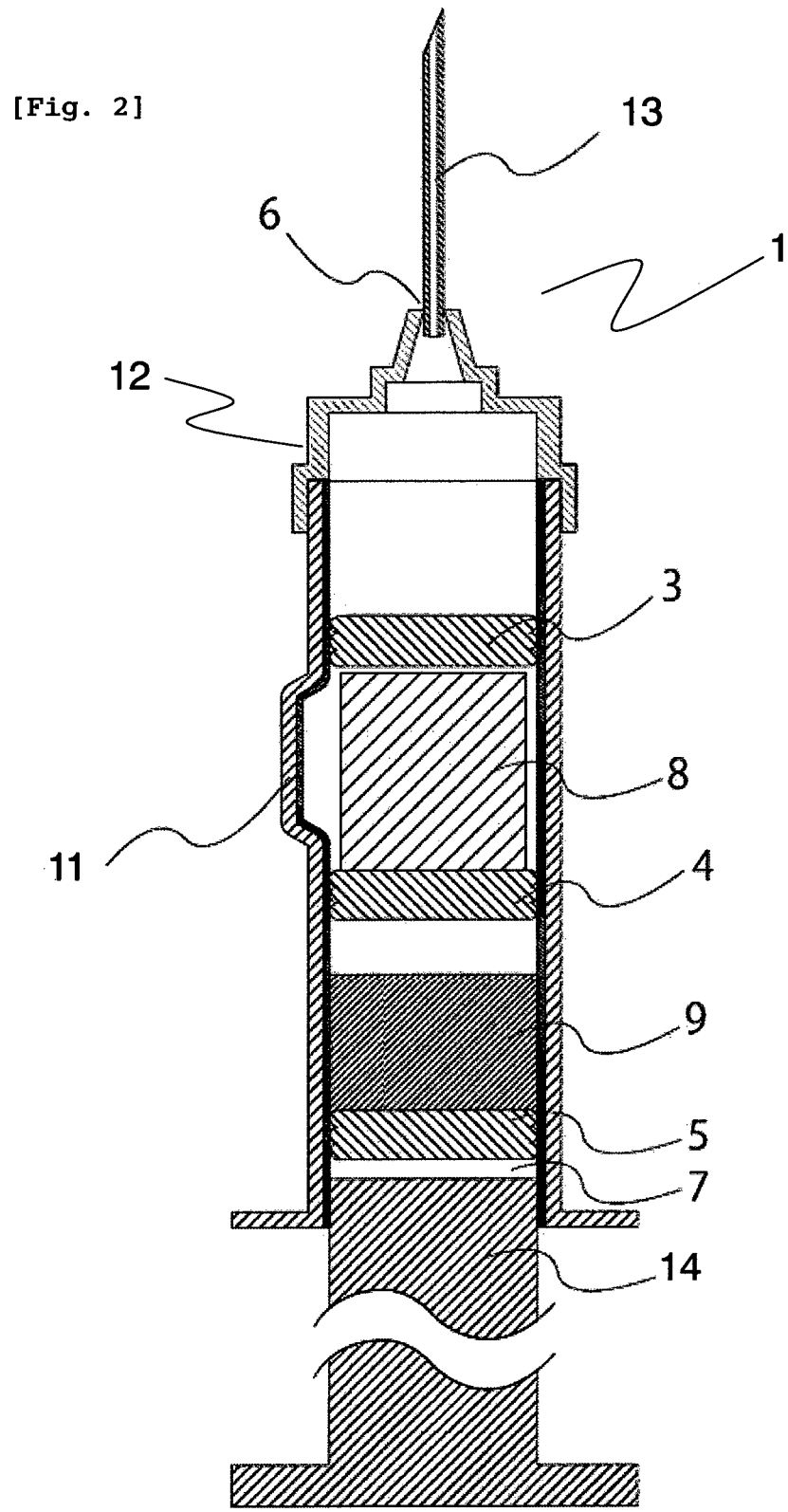

[Fig. 3]
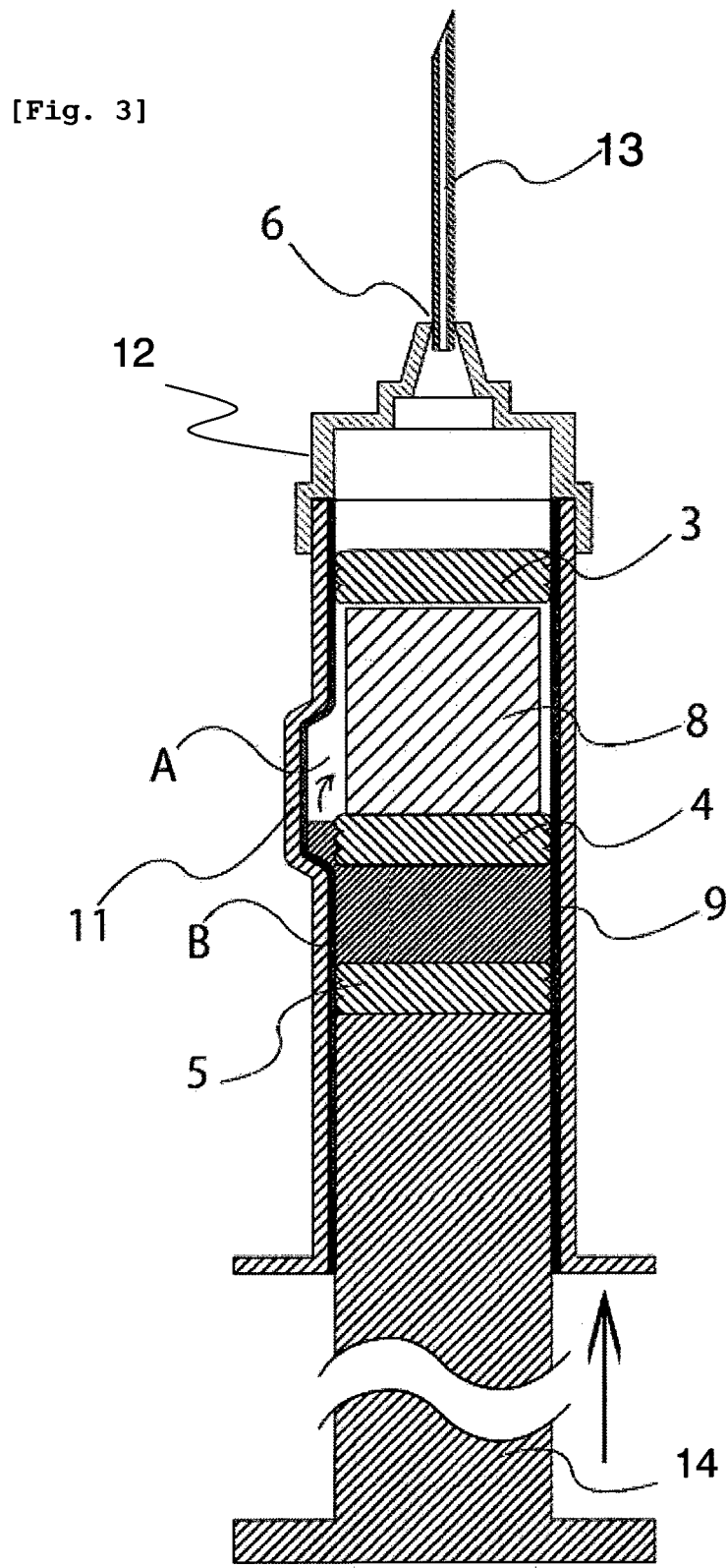

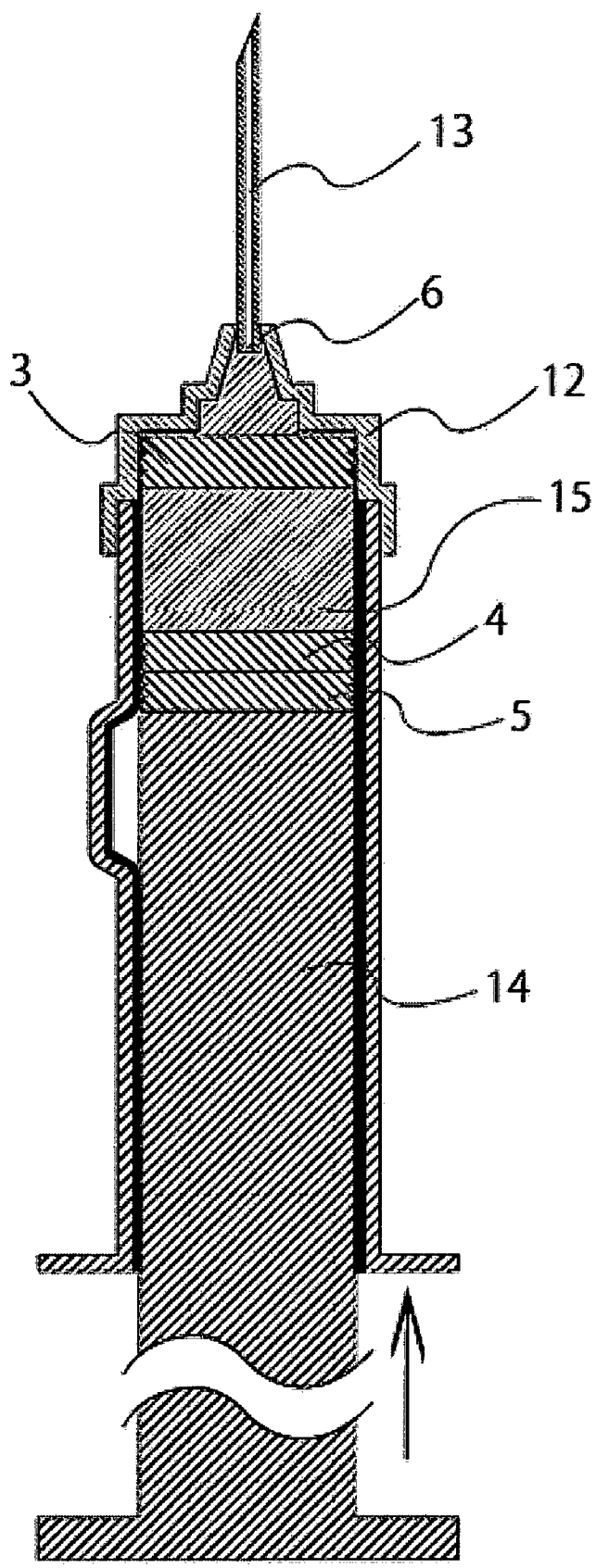
[Fig. 4]

[Fig. 5]
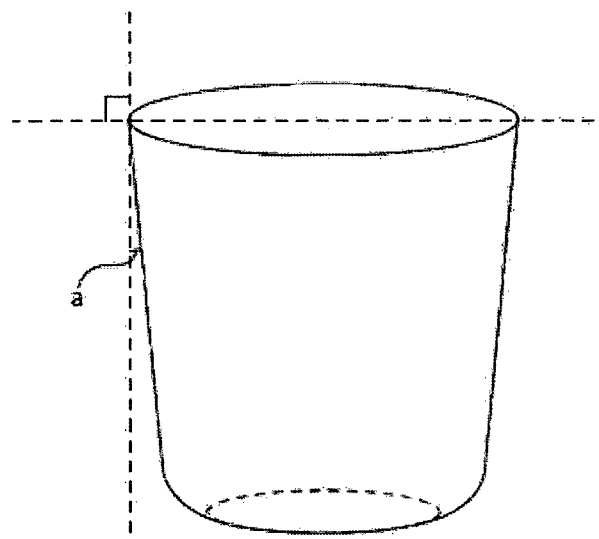
[Fig. 6]
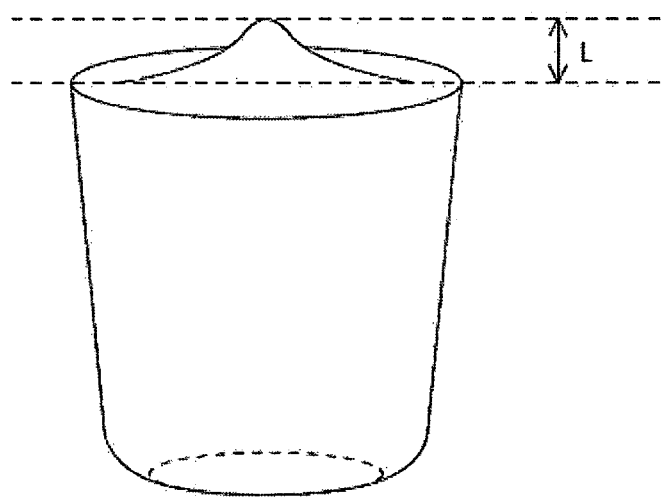

[Fig. 7]
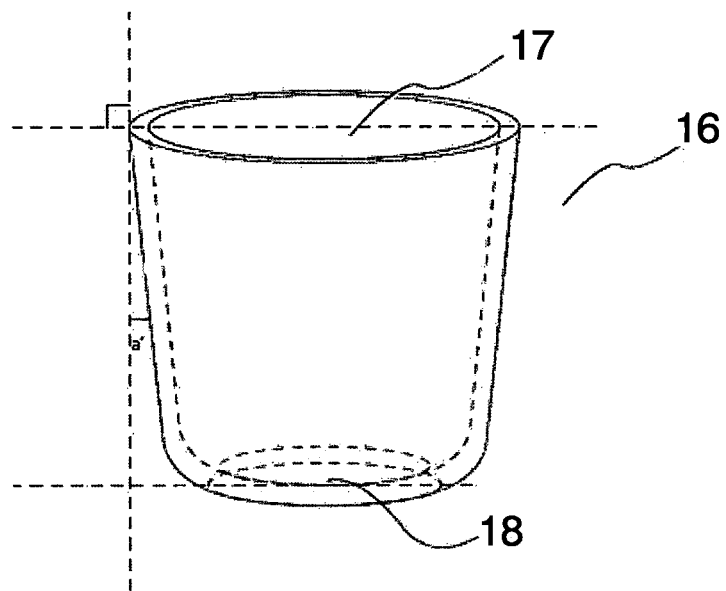
[Fig. 8]
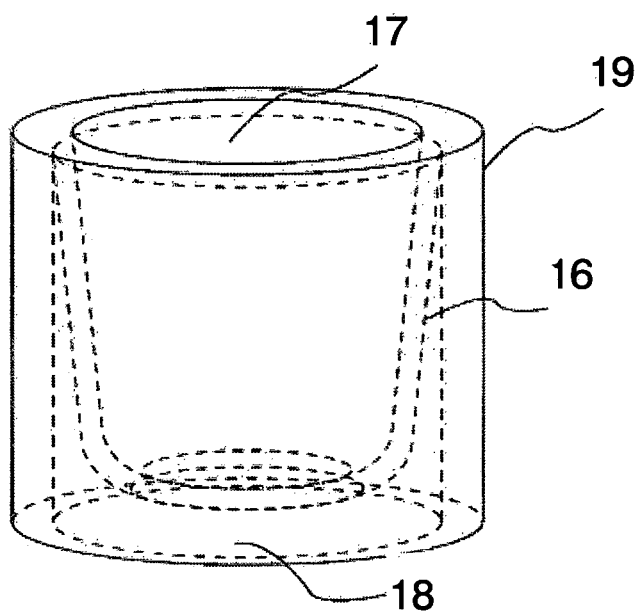

[Fig. 9]
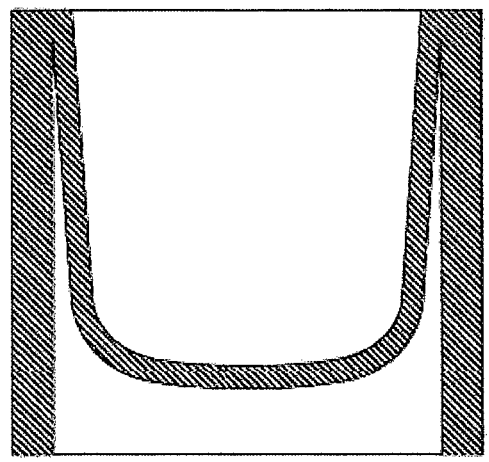
[Fig. 10]
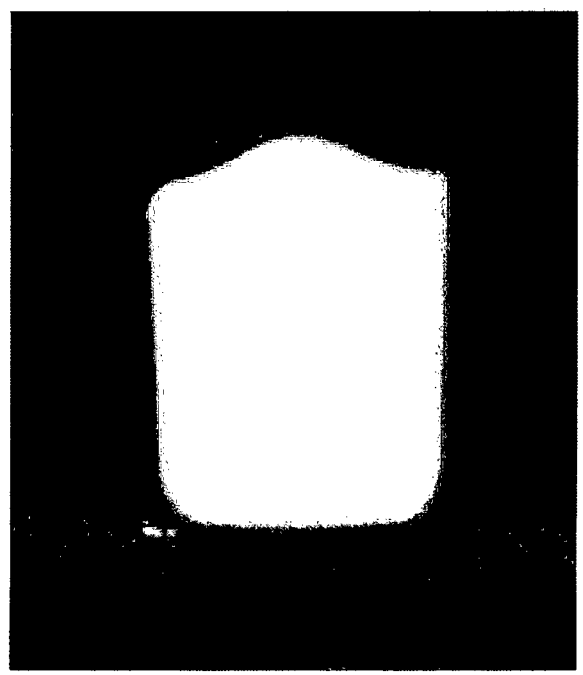

[Fig. 11]

MEDICAL DEVICE CONTAINING A CAKE COMPOSITION COMPRISING ARIPIPRAZOLE AS AN ACTIVE INGREDIENT, AND A CAKE COMPOSITION COMPRISING ARIPIPRAZOLE AS AN ACTIVE INGREDIENT

TECHNICAL FIELD

The present invention relates to a medical device equipped with a storage container containing a separately prepared freeze-dried cake composition comprising aripiprazole as an active ingredient, wherein there is a space between an inner wall of the storage container and the cake composition, and a cake composition comprising aripiprazole as an active ingredient and having a specific strength.

BACKGROUND ART

Aripiprazole, which is used as an active ingredient in pharmaceutical compositions, is known as an atypical antipsychotic useful for the treatment of schizophrenia, and is represented by the following structural formula:

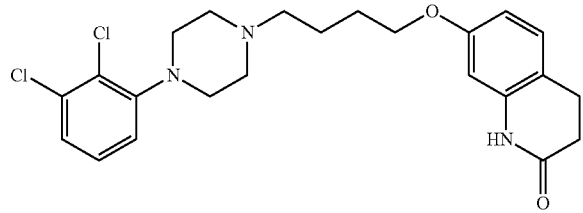 [SMILES: O=C1CCc2ccc(OCCCCN3CCN(c4cccc(Cl)c4Cl)CC3)cc2N1]

A pharmaceutical composition comprising aripiprazole as an active ingredient is used, for example, by the following method: the pharmaceutical composition is suspended in a dispersion medium, and the thus-obtained suspension is freeze-dried, thereby preparing a cake composition. The cake composition is mixed with a desired dispersion medium (injection liquid) and thereby resuspended at the time of use. The resuspension is then intramuscularly or subcutaneously injected (for example, see Patent Literature 1 and 2).

Such a cake composition is produced by freeze-drying a medical fluid in a medical device such as a syringe, which also serves as a storage container (for example, see Patent Literature 3). Additionally, Patent Literature 3 employs a form, a so-called dual-chamber syringe, in which after a solution is freeze-dried to prepare a freeze-dried substance in a syringe, the syringe is sealed by a stopper, and further, an injection liquid is enclosed in a separate chamber in the syringe.

The medical device having a syringe-like shape has a syringe tube whose inner wall is treated with silicone so as to allow a sealing plug, such as a stopper, to smoothly slide in the syringe tube.

However, when a freeze-dried substance is prepared in a storage container by enclosing a medical fluid of a pharmaceutical composition and freeze-drying the medical fluid in the storage container, the freeze-dried substance comes into contact with the silicone-treated inner wall of the storage container, and the silicone used for treating the inner wall of the storage container may be mixed into the freeze-dried substance due to a long period (several months) of storage.

CITATION LIST

Patent Literature

PTL 1: U.S. Pat. No. 5,006,528
PTL 2: Japanese Unexamined Patent Publication No. 2007-509148
PTL 3: Japanese Unexamined Patent Publication No. H8-112333

SUMMARY OF INVENTION

Technical Problem

When a freeze-dried substance was prepared in a storage container whose inner wall had been treated with silicone by enclosing a suspension (dispersion) of a pharmaceutical composition comprising aripiprazole as an active ingredient and freeze-drying the suspension (dispersion) in the storage container, and when the silicone was mixed into the freeze-dried substance due to a long period (several months) of storage and the mixture was resuspended in a dispersion medium, the phenomenon of agglomeration of aripiprazole in the suspension was observed. Specifically, it became clear that there is a problem in that the presence of silicone causes an increase in the mean particle size of aripiprazole in the resuspension.

Such agglomeration of aripiprazole results in a reduced dissolution rate because the contacted area of the particles does not contribute to dissolving the particles. When the dissolution rate changes as described above, it results in a dissolution profile in which blood levels differ between the aripiprazole dispersion in the suspension before being subjected to freeze-drying and the aripiprazole dispersion in the suspension obtained by resuspending the freeze-dried substance. This considerably affects the drug efficacy, and poses serious problems as follows: the medicinal properties of aripiprazole are unable to sufficiently exhibit their efficacy; clogging occurs when the drug is used in an injection form; and physical stimulus occurs at the injection site due to increased particle size.

An object of the present invention is to provide, with respect to the above problems, a medical device containing a cake composition comprising aripiprazole as an active ingredient and capable of suppressing the agglomeration of aripiprazole in a suspension obtained by resuspending a freeze-dried substance; and a cake composition comprising aripiprazole as an active ingredient.

Solution to Problem

The present inventors conducted extensive studies in order to solve the above problem and, as a result, found that providing a space between the silicone-treated inner wall of the storage container and the cake composition makes it possible to reduce the frequency of contact between the silicone and the cake composition, and to suppress the mixing of the silicone into the suspension when the cake composition is resuspended. The present inventors also found a cake composition that can inhibit the breaking of the cake composition in the storage container, which is caused by external physical impacts; reduce the frequency of contact with the silicone used for treating the inner wall; and quickly resuspend in a dispersion medium.

The present invention has been accomplished through further studies based on the above findings.

Item 1. A medical device containing a separately prepared freeze-dried cake composition comprising aripiprazole as an active ingredient in a storage container whose inner wall is treated with silicone, wherein there is a space between the inner wall and the cake composition.

Item 2. The medical device containing the cake composition according to Item 1, wherein the cake composition is a mass that was freeze-dried in a container separate from the storage container.

Item 3. The medical device containing the cake composition according to Item 1 or 2, wherein the apparent volume of the cake composition accounts for 30 to 99% of the volume of the storage container.

Item 4. The medical device containing the cake composition according to any one of Items 1 to 3, wherein the cake composition has a cylindrical shape.

Item 5. The medical device containing the cake composition according to Item 4, wherein a top surface of the cylindrical cake composition is raised.

Item 6. The medical device containing the cake composition according to Item 4 or 5, wherein a side surface of the cylindrical cake composition is sloped.

Item 7. The medical device containing the cake composition according to any one of Items 1 to 6, wherein the storage container treated with silicone is a vial or syringe.

Item 8. The medical device containing the cake composition according to Item 7, wherein the syringe has multiple chambers and the cake composition is contained in at least one chamber.

Item 9. The medical device containing the cake composition according to Item 7, wherein the syringe has a chamber (A) for containing the cake composition, and a chamber (B) for containing an injection liquid;
the chamber (A) is arranged on the side where a needle is placed, and the chamber (B) is arranged on the side where a plunger is placed; and
the cake composition is contained in the chamber (A) and the injection liquid is contained in the chamber (B).

Item 10. The medical device containing the cake composition according to any one of Items 1 to 9, wherein the cake composition has a strength of 5 to 100 N.

Item 11. A cake composition comprising aripiprazole as an active ingredient and having a strength of 5 to 100 N.

Item 12. The cake composition according to Item 11, wherein the percentage of aripiprazole in the cake composition is 60 to 95% by mass.

Item 13. The cake composition according to Item 11 or 12, wherein the amount of aripiprazole in the cake composition is 0.1 to 0.6 g.

Item 14. The cake composition according to any one of Items 11 to 13, obtained by freeze-drying 0.25 to 12 g of a suspension having an aripiprazole solids content of 5 to 45% by mass.

Item 15. The cake composition according to any one of Items 11 to 14, wherein the cake composition has a cylindrical shape.

Item 16. The cake composition according to Item 15, wherein a top surface of the cylindrical cake composition is raised.

Item 17. The cake composition according to Item 15 or 16, wherein a side surface of the cylindrical cake composition is sloped.

Item 18. The cake composition according to any one of Items 11 to 17, wherein the cake composition is used for being placed in a medical device.

Item 19. The cake composition according to Item 18, wherein the cake composition is a mass that was freeze-dried in a container separate from a storage container in the medical device.

Item 20. A method for producing a medical device containing a cake composition comprising aripiprazole as an active ingredient, the method comprising
a step of enclosing a separately prepared freeze-dried cake composition comprising aripiprazole as an active ingredient in a storage container whose inner wall is treated with silicone.

Item 21. The method for producing the medical device according to Item 20, wherein the storage container treated with silicone is a vial or syringe.

Item 22. The method for producing the medical device according to Item 21, wherein the syringe has multiple chambers and the cake composition is contained in at least one chamber.

Item 23. The method for producing the medical device according to Item 22, wherein the syringe has a chamber (A) for containing the cake composition, and a chamber (B) for containing an injection liquid;
the chamber (A) is arranged on the side where a needle is placed, and the chamber (B) is arranged on the side where a plunger is placed; and
the cake composition is contained in the chamber (A) and the injection liquid is contained in the chamber (B).

The medical device recited in the above method for producing a medical device is a medical device according to any one of Items 1 to 10.

Item 24. A method for producing a cake composition comprising aripiprazole as an active ingredient and having a strength of 5 to 100 N, the method comprising
a step of freeze-drying a suspension comprising aripiprazole as an active ingredient.

The cake composition recited in the above method for producing a cake composition is a cake composition according to any one of Items 11 to 19.

The medical device containing a cake composition and the cake composition of the present invention are described in detail below.

The present invention relates to a medical device containing a separately prepared freeze-dried cake composition comprising aripiprazole as an active ingredient, in a storage container whose inner wall is treated with silicone.

As used herein, the "cake" in the cake composition means a dried solid that maintains the shape of the liquid before being dried. For example, when a vial that has a columnar inner shape is used, the cake is a dried solid that maintains the columnar shape.

The cake composition of the present invention comprising aripiprazole as an active ingredient can be produced by freeze-drying a suspension comprising aripiprazole as an active ingredient.

The cake composition is enclosed in a storage container whose inner wall is treated with silicone, thereby allowing a space to be provided between the storage container and the cake composition. Providing a space between the silicone-treated inner wall of the storage container and the cake composition as described above makes it possible to suppress an increase in the mean particle size of aripiprazole, which is caused by mixing of the silicone into the cake composition when the cake composition that has been stored for a long period of time is resuspended in a dispersion medium. In other words, providing a space can suppress the agglomeration of aripiprazole particles.

When a cake composition is produced by placing the suspension in a conventional storage container and freeze-drying the suspension therein, the cake composition adheres to the inner wall of the storage container treated with silicone. Therefore, when the cake composition is resuspended, a large amount of the silicone is mixed into the suspension. This undesirably causes an increase in the mean particle size of aripiprazole, which is an active ingredient.

The treatment with silicone is performed on the inner wall of the storage container. When the storage container is a vial, for example, the inner wall of the storage container means the inner side surface of the vial. When the storage container is a syringe, the inner wall means the inner surface of the syringe tube. In the vial, treating the inner wall with silicone provides functions to reduce the amount of medical fluid remaining on the inner surface of the vial and to minimize the amount of the medical fluid inserted therein. Further, in the syringe, treating the inner wall with silicone provides a function as a lubricant for sliding a plunger and stoppers (sealing plugs) provided in the syringe tube.

Treatment with silicone means to apply and adhere silicone to the inner wall of the storage container and, if necessary, dry the surface to which the silicone is applied.

A vial, syringe or the like is used as a storage container that is treated with silicone. In the case of a syringe, a prefilled syringe in which the cake composition is enclosed is used. Therefore, the syringe itself also serves as a storage container. Further, as a syringe, a single-chamber syringe or a syringe having multiple chambers in which a cake composition is contained in one of the chambers (hereinafter also referred to as dual-chamber syringe) is used.

A dual-chamber syringe comprises a chamber (A) for containing a cake composition and a chamber (B) for containing an injection liquid (liquid for injection), and has a structure in which the chamber (A) is arranged on the side where a needle is placed and the chamber (B) is arranged on the side where a plunger is placed. The dual-chamber syringe is described below, with reference to the figures.

FIG. 1 is a cross-section view showing an embodiment of a dual-chamber syringe. A dual-chamber syringe 1 comprises the following stoppers (sealing plugs) in a syringe tube 2, in the described order from the side where a needle is placed (i.e., an end 6 side where a needle is placed): a front stopper 3, a middle stopper 4 and an end stopper 5. The chamber A is defined by the front stopper 3 and the middle stopper 4, and the chamber B is defined by the middle stopper 4 and the end stopper 5. The front stopper 3 may be dispensed with. A front assembly 12 that houses the front stopper 3 when the syringe is used is provided to the end 6 side. When the front stopper 3 is not provided, the syringe 1 may have a common shape in which the end of the syringe 1 but not the front assembly is molded in a form to which a needle is attached. When the front stopper 3 is provided, the front stopper 3 is housed in the front assembly 12, and a space is created between the front stopper 3 and the front assembly 12, thereby forming a passage for discharging a suspension obtained by resuspending a cake composition 8 in an injection liquid 9 through the end 6.

The cake composition 8 is enclosed in the chamber (A), and the injection liquid 9 for resuspending the cake composition 8 is enclosed in the chamber (B). Additionally, the inner wall of the syringe tube 2 is treated with silicone 10. Further, a bypass 11 having a shape that externally protrudes from the inside of the side surface of the syringe tube is provided to transfer the injection liquid 9 to the chamber (A) in which the cake composition 8 is enclosed. The bypass 11 is provided toward the end 6 side from the middle stopper 4. During storage, the injection liquid 9 is prevented from flowing into the chamber (A) side.

The dual-chamber syringe 1 may comprise one bypass 11 or multiple bypasses 11.

The usage form of the dual-chamber syringe 1 when it is used as a medical device of the present invention is explained with reference to the attached FIGS. 2 to 4.

A needle 13 is inserted into the end 6 of the dual-chamber syringe 1, and a plunger 14 is inserted into an opening 7 (see FIG. 2).

The plunger 14 is pressed into the end 6 side from the opening 7, and the end stopper 5 is thereby slid to the end 6 side. By further pressing in the plunger 14, the middle stopper 4 and the front stopper 3 are also slid as the end stopper 5 is slid. When the middle stopper 4 reaches the bypass 11, the injection liquid 9 is flowed through the bypass 11 into the chamber (A) in which the cake composition 8 is enclosed (see FIG. 3).

The cake composition in the chamber (A) is resuspended by the injection liquid 9 that flowed therein, thereby giving a suspension 15. Further, the front stopper 3 is housed in the front assembly 12 as the plunger 14 is pressed in, and the resuspension 15 is discharged from the end 6 into which the needle 13 is inserted, through the space created between the front stopper 3 and the front assembly 12 (see FIG. 4).

The length of the syringe tube in the syringe (the length in which the stopper may be located) is preferably about 50 to 200 mm and more preferably about 70 to 110 mm.

Further, the distance from the center of the front stopper to the center of the middle stopper is preferably about 5 to 40 mm and more preferably about 15 to 35 mm. The distance between the center of the middle stopper to the center of the end stopper is preferably about 2 to 50 mm and more preferably about 10 to 30 mm.

Further, the inner diameter of the syringe tube is preferably about 5 to 30 mm and more preferably about 10 to 20 mm.

The thus-configured dual-chamber syringe is preferable from the viewpoint that a cake composition and a dispersion medium (injection liquid) for resuspending the cake composition can be simultaneously enclosed in such a dual-chamber syringe and the step of injecting a dispersion medium (injection liquid) can therefore be omitted at the time of use.

When a single-chamber syringe is used as the storage container, an injection liquid is introduced into the syringe from the outside at the time of use, and the cake composition is thereby resuspended for use.

The shape of the cake composition enclosed in the storage container is not particularly limited, insofar as a space is created between the inner wall of the storage container and the cake composition. When the storage container is cylindrical like a syringe tube, for example, the cake composition is preferably formed in a cylindrical shape.

When the cake composition is cylindrical, it is preferable that the container (which is separate from the storage container) that is used for freeze-drying the cake composition be molded using plastic so that the cake composition can be easily removed from the container, and that the side of the container be further sloped as shown in FIG. 5, for ease in molding the part that will be in contact with a liquid. When the cake composition is shaped so as to have the above-described slope, the angle ("a" in FIG. 5) of the slope is preferably about 0.1 to 10 degrees and more preferably about 0.5 to 3 degrees. The slope may be formed partially or entirely around the circumference.

Further, as shown in FIG. 6, the top surface of the cylindrical cake composition is raised. This provides an effect of reducing the contact area with the storage container (for example, in the case of the dual-chamber syringe, the contact with the front stopper or the middle stopper is reduced). The distance ("L" in FIG. 6) between the peak of the raised portion and the top surface is preferably about 0.5 to 5 mm and more preferably about 1 to 3 mm.

The cylindrical cake composition may have a raised circumference to enable the contact area with the storage container to be reduced (for example, in the case of the dual-chamber syringe, to reduce the contact with the front stopper or the middle stopper).

The apparent volume of the cake composition preferably accounts for about 30% or more, more preferably about 40% or more and still more preferably 50% or more of the volume of the storage container, from the viewpoint of inhibiting the breaking of the cake composition due to impact with the inner wall of the storage container during production and transport of the medical device of the present invention, and shortening the overall length of the syringe. Further, the apparent volume of the cake composition is preferably about 99% or less, more preferably about 90% or less and still more preferably 80% or less, from the viewpoint of reducing the frequency of adhesion of the cake composition to the silicone used for treating the inner wall of the storage container.

The term "apparent volume" means the volume of the cake composition when the cake composition is regarded as a mass without microscopic pores, spaces, cracks, and the like.

Further, the volume of the storage container refers to the volume occupied by the portion in which the cake composition is enclosed. For example, in the case of the below-described dual-chamber syringe having multiple chambers, the volume of the storage container means the volume of the chamber portion (chamber (A)) in which the cake composition is enclosed.

The specific apparent volume of the cake composition is preferably about 250 to 12,000 mm$^3$, more preferably about 500 to 5,000 mm$^3$ and still more preferably 800 to 1,600 mm$^3$.

Further, the volume of the storage container is preferably about 250 to 40,000 mm$^3$, more preferably about 500 to 17,000 mm$^3$ and still more preferably 800 to 5,300 mm$^3$.

The cake composition is obtained in the following manner: a cake composition is separately obtained by preparing a suspension composition comprising aripiprazole as an active ingredient and further freeze-drying the suspension composition, and the separately obtained cake composition is transferred to the storage container. Therefore, it is preferable to freeze-dry the suspension in a container separate from the storage container to produce a mass of the cake composition, and to transfer the mass to the storage container.

Plastic is preferable as a material for the separate container, with olefin-based resin and the like, for example, being more preferable from the following viewpoints: although the resulting cake composition slightly expands when freeze-dried in the production of the cake composition, the expansion does not result in strong adhesion between the cake composition and the container, or even if adhesion occurs between the cake composition and the container, the cake composition can be easily removed from the container by deforming the container; when the suspension must be aseptically prepared, the container can be easily molded in an aseptic atmosphere and easily sterilized by radiation; and such materials are low in cost and disposable. Non-limiting examples of olefin resin include polyethylene-based resin, polypropylene-based resin, and the like.

The shape of the container (which is separate from the storage container), that is used for producing the cake composition, is suitably determined depending on the shape of the cake composition. Hereinbelow, a method for producing a cylindrical cake composition is described with reference to the figures, based on the shape of the container.

FIG. 7 is a schematic view showing the shape of the container (Which is separate from the storage container) used for producing the cylindrical cake composition. The container 16 has an opening 17 on the top. The suspension is poured through the opening 17 and freeze-dried, thereby molding a cake composition in the container 16. The molded cake composition can be easily removed from the container 16 by pressing the bottom surface 18. The inner surface of the container is preferably sloped to facilitate removal of the cake composition. The angle (a' in FIG. 7) is the same as the angle of the resulting cake composition. The angle is preferably about 0.1 to 10 degrees and more preferably about 0.5 to 3 degrees. The slope may be formed partially or entirely around the circumference.

Further, the bottom surface of the container (which is separate from the storage container) is preferably raised so that the contact area with the storage container can be reduced (for example, in the case of the dual-chamber syringe, the contact with the front stopper or the middle stopper is reduced) and the freeze-dried cake can be easily removed from the container (which is separate from the storage container).

Further, in order to allow the resulting cake composition to be easily removed by pressing the bottom surface 18, the container may be provided with an exterior frame 19 as shown in the schematic view of FIG. 8 and in the cross-section view of FIG. 9.

Examples of silicone applied to the inner surface of the storage container include silicone oil or a silicone derivative that is used in known medical applications. Specifically, the silicone is a linear polymer having a siloxane bond as a skeleton with a $C_{1-6}$ alkyl group on the side chain. More specifically, the silicone may be one with the repeating unit represented by the following Formula (I):

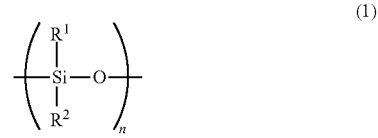

(1)

In Formula (I), $R^1$ and $R^2$ are the same or different, and each represents a hydrogen atom or a $C_{1-6}$ hydrocarbon group, where n is an integer of 1 to 1,000. Specific examples of the hydrocarbon groups represented by $R^1$ and $R^2$ include a methyl group, an ethyl group, a propyl group, a butyl group, a pentyl group, and a hexyl group. When n is 2 or more, the repeating units may be the same or different.

Specific examples of the silicone oil include dimethyl polysiloxane. The silicone oil derivative may be one in which the substituent on the side chain of the silicone, and/or some of the terminal Si substituents are replaced with, for example, a polyoxyalkylene group or a vinyl group.

The silicone oil and silicone oil derivative can be obtained from commercially available products, for example, Shin-Etsu Silicone KM72® and Shin-Etsu Silicone KF96ADF®, both produced by Shin-Etsu Chemical Co., Ltd., and Dow Corning® (produced by Dow Corning Corporation). An emulsion (Dow Corning® 365, 35% Dimethicone NF Emulsion (produced by Dow Corning Corporation)) that contains a surfactant and water, can also be used as the silicone oil.

The average molecular weight of the silicone is not particularly limited, and is preferably from 10 to 100,000,000, more preferably from 100 to 10,000,000, and still more preferably from 200 to 10,000.

The mean particle size of the aripiprazole contained in the cake composition that is stored in the storage container is preferably 0.1 µm or larger, more preferably 0.5 µm or larger, and still more preferably 1.5 µm or larger when it is used as a sustained-release injectable preparation, because a sustained release lasting as long as 1 month can be desirably obtained with these ranges. From the standpoint of slowing settling, improving ease of manufacture, and preventing needle clogging during injection when, for example, a prefilled syringe is used as the storage container, the mean particle size of the aripiprazole in the cake composition is preferably smaller than 200 µm, more preferably smaller than 10 µm, and still more preferably about 4 µm or smaller.

Here, the "mean particle size" refers to a volume mean diameter as measured by a laser diffraction scattering method. The particle distribution is measured using a laser diffraction scattering method, and the mean particle size is calculated based on the particle distribution.

From the viewpoint of attaining sufficient strength to allow the cake composition to be removed from the container used for freeze drying, which is separate from the storage container, the content of the aripiprazole in the cake composition is preferably about 60% by mass or more, more preferably about 65% by mass or more, and still more preferably about 70% by mass or more. Furthermore, the content of the aripiprazole in the cake composition is preferably about 95% by mass or less, more preferably about 90% by mass or less, and still more preferably about 80% by mass or less in order to stabilize the dispersion of the aripiprazole in a liquid containing a suspending agent and the like.

The amount of the aripiprazole contained in the cake composition is preferably about 0.1 g or more, and more preferably about 0.15 g or more, and still more preferably about 0.2 g or more from the viewpoint of the dose that is necessary to maintain the effective blood concentration required in the treatment after administration into the body. Furthermore, the amount of the aripiprazole contained in the cake composition is preferably about 0.6 g or less, more preferably about 0.55 g or less, and still more preferably about 0.5 g or less from the viewpoint of safety with respect to the physical stimulus to the body when administered at one time.

The aripiprazole contained in the cake composition is known to exist in a variety of crystal forms, including monohydrates (aripiprazole hydrate A), and many anhydrous forms, specifically, such as anhydrous crystal B, anhydrous crystal C, anhydrous crystal D, anhydrous crystal E, anhydrous crystal F, and anhydrous crystal G. All of these forms may be used in the cake composition of the present invention.

The cake composition of the present invention may also appropriately contain other components, such as a suspending agent, a bulking agent, a buffer, a pH adjuster, an excipient, a lubricant, a fluidizer, a disintegrant, a binder, a surfactant, a preservative, a flavoring agent, an odor improving agent, and a tonicity agent, in addition to the aripiprazole that is used as an active ingredient.

The additives may be those disclosed in Japanese Unexamined Patent Publication No. 2007-509148 (Translation of WO2005/041937).

The content of the suspending agent in the cake composition is preferably about 0.1 to 10% by mass and more preferably about 1 to 5% by mass. Preferable examples of suspending agents include sodium carboxymethylcellulose, hydroxypropylcellulose, carboxymethylcellulose, hydroxypropylethylcellulose, hydroxypropylmethylcellulose, and polyvinylpyrrolidone, or a mixture of two or more of these. However, the suspending agent is not limited to these, and sodium carboxymethylcellulose and polyvinylpyrrolidone can preferably be used.

Examples of other suspending agents suited for use as the vehicle for the aripiprazole include various polymers, low molecular oligomers, natural products, and surfactants (both nonionic and ionic). Specific examples include cetylpyridinium chloride, gelatin, casein, lecithin (phosphatide), dextran, glycerol, gum acacia, cholesterol, tragacanth, stearic acid, benzalkonium chloride, calcium stearate, glyceryl monostearate, cetostearyl alcohol, cetomacrogol emulsifying wax, sorbitan ester, polyoxyethylenealkyl ether (for example, a macrogol ether such as cetomacrogol 1000), a polyoxyethylene castor oil derivative, and a polyoxyethylenesorbitan fatty acid ester (for example, commercially available Tweens®, including Tween20® and Tween80® (produced by ICI Specialty Chemicals)). Other examples include polyethylene glycols (for example, Carbowaxes 3350® and 1450®, and Carbopol 934® (produced by Union Carbide)), dodecyltrimethylammonium bromide, polyoxyethylene stearate, colloidal silicon dioxide, phosphate, sodium dodecyl sulfate, carboxymethylcellulose calcium, hydroxypropylcellulose (for example, HPC, HPC-SL, and HPC-L), methylcellulose, hydroxyethylcellulose, hydroxypropylcellulose, hydroxypropylmethyl-cellulose phthalate, noncrystalline cellulose, magnesium aluminum silicate, triethanolamine, polyvinyl alcohol (PVA), ethylene oxide-formaldehyde 4-(1,1,3,3-tetramethylbutyl)-phenol polymers (also known as tyloxapol, superione, and triton), poloxamers (for example, Pluronics F68® and F108®, which are block copolymers of ethylene oxide and propylene oxide); poloxamine (also known as, for example, Tetronic 908® and Poloxamine 908®, which are tetrafunctional block copolymers derived from the continuous addition of propylene oxide and ethylene oxide to ethylenediamine (produced by BASF Wyandotte Corporation, Parsippany, N.J.); charged phospholipids, such as dimyristoylphosphatidylglycerol and dioctylsulfosuccinate (DOSS); Tetronic 1508® (T-1508; produced by BASF Wyandotte Corporation), dialkyl esters of sodium sulfosuccinate (for example, Aerosol OT®, which is a dioctyl ester of sodium sulfosuccinate (produced by American Cyanamid)); Duponol P® (a sodium lauryl sulfate; produced by DuPont); Tritons X-200® (an alkylarylpolyether sulfonate; produced by Rohm and Haas); Crodestas F-110® (a mixture of sucrose stearate and sucrose distearate; produced by Croda Inc.); p-isononylphenoxypoly-(glycidol) (also known as Olin-10G® or Surfactant 10-G® (Olin Chemicals, Stamford, Conn.)); Crodestas SL-40® (produced by Croda, Inc.); SA90HCO ($C_{18}H_{37}CH_2(CON(CH_3))—CH_2(CHOH)_4(CH_2OH)_2$ (produced by Eastman Kodak Co.); decanoyl-N-methylglucamide; n-decyl-β-D-glucopyranoside; n-decyl-β-D-maltopyranoside; n-dodecyl-β-D-glucopyranoside; n-dodecyl-β-D-maltoside; heptanoyl-N-methylglucamide; n-heptyl-β-D-glucopyranoside; n-heptyl-β-D-thioglucoside; n-hexyl-β-D-glucopyranoside; nonanoyl-N-methylglucamide; n-nonyl-β-D-glucopyranoside; octanoyl-N-methylglucamide; n-octyl-β-D-glucopyranoside; and octyl-β-D-thioglucopyranoside.

Most of these suspending agents are known pharmaceutical excipients, and are described in detail in the Handbook of Pharmaceutical Excipients, co-published by the American Pharmaceutical Association and The Pharmaceutical Society of Great Britain (The Pharmaceutical Press, 1986), which is specifically incorporated herein by reference. The suspending agents are commercially available, and can be produced by techniques known in the art.

The content of the bulking agent (also called a cryogenic/lyophilize protecting agent) in the cake composition is preferably about 5 to 40% by mass, more preferably about 10 to 30% by mass, and still more preferably about 15 to 25% by mass. The bulking agent may be selected from, for example, mannitol, sucrose, maltose, xylitol, glucose, starch, and sorbitol, or a mixture of two or more of these. However, the bulking agent is not limited to these, and mannitol can be preferably used.

Preferable examples of buffers include sodium phosphate, disodium hydrogen phosphate, sodium dihydrogen phosphate, potassium phosphate, and TRIS buffer, or a mixture of two or more of these. However, the buffer is not limited to these, and sodium phosphate, disodium hydrogen phosphate, and sodium dihydrogen phosphate are preferably used.

When the cake composition is formed into a suspension by being dispersed in a dispersion medium at the time of use, the pH adjuster is used to adjust the pH of the aripiprazole suspension to about 6 to 7.5, preferably about 7. When the pH of the suspension obtained by dispersing the cake composition in a dispersion medium is higher than the desired value, i.e., about 7, an acidic pH adjuster is used. When the pH of the suspension is lower than the desired value, i.e., about 7, a basic pH adjuster is used. As the acidic pH adjuster, hydrochloric acid or acetic acid, preferably hydrochloric acid is used. Examples of basic adjusters include sodium hydroxide, potassium hydroxide, calcium carbonate, magnesium oxide, and magnesium hydroxide. Among these, sodium hydroxide is preferably used.

The suspension comprising aripiprazole before freeze-drying as an active ingredient, which is the suspension being used for preparing the cake composition, can be obtained by mixing a dispersion medium with a composition suitably comprising the aripiprazole (i.e., the active ingredient), the aforementioned suspending agent, bulking agent, buffer, pH adjuster, excipient, lubricant, fluidizer, disintegrant, binder, surfactant, preservative, flavoring agent, odor improving agent, tonicity agent and the like in such a manner that the contents thereof will be in the desirable ranges described above.

As the dispersion media, water, or a hydrous solvent containing water and an organic solvent is used. The organic solvent is one that is miscible with water. Examples thereof include alcohols, such as methanol, ethanol, propanol, and isopropanol; ketones, such as acetone; ethers, such as tetrahydrofuran; dimethylformamide; and mixtures thereof. Of these, ethanol is particularly preferred. The amount of water used for the hydrous solvent is not particularly limited, and is, for example, preferably at least 10% by mass of the solvent.

Preferably, a wet pulverization technique is used, and the dispersed aripiprazole particles are subjected to pulverization in the presence of a pulverization medium to have a desired mean particle size.

Preferably, an antiseptic wet pulverization technique, such as wet ball milling, high-pressure homogenization, or high-shear homogenization is used. In addition to these pulverization techniques, a low-energy or high-energy mill (for example, a roller mill) can also be used.

Use of, for example, controlled crystallization is also possible.

A homogeneous suspension of aripiprazole having a desired mean particle size can be obtained by using the above-mentioned methods.

The mean primary particle size of the aripiprazole in the suspension is preferably 0.1 μm or larger, more preferably 0.5 μm or larger, and still more preferably 1.5 μm or larger in a sustained-release injectable preparation, because a sustained release lasting as long as one month can be desirably obtained with these ranges. From the standpoint of slowing settling, improving ease of manufacture, and preventing needle clogging during injections, the mean particle size of the aripiprazole in the suspension is preferably smaller than 200 μm, more preferably smaller than 10 μm, and still more preferably about 4 μm or smaller.

The "mean particle size" can be measured using the same method that was used to measure the cake composition. The term "primary particle size" refers to the particle size of each individual particle, not the particle size of agglomerated particles.

The "mean particle size" refers to a volume mean diameter as measured by a laser-light scattering method (LLS). The particle distribution is measured by LLS, and the mean particle size is calculated based on the particle distribution.

Aripiprazole with the desired mean primary particle size can be produced by using preferably, for example, an impinging jet crystallization method (see Japanese Unexamined Patent Publication No. 2007-509153 (Translation of WO2005/041970) filed by Bristol-Myers Squibb), or a wet pulverization method that uses a high-pressure homogenizer (see Japanese Patent Application No. 2007-200088 filed by Otsuka Pharmaceutical Co., Ltd.).

The crystal forms of the aripiprazole that is contained in the suspension may be the same as those of the aripiprazole contained in the cake composition.

The solids content of the aripiprazole in the suspension is preferably about 5% by mass or more, more preferably about 10% by mass or more, and still more preferably about 20% by mass or more, since having such a solids content reduces the size of the syringe by reducing the volume of the cake after freeze-drying, imparts strength to the cake to resist the generation of fine particles, and enables administration with a smaller dose. Furthermore, the solids content of the aripiprazole in the suspension is preferably about 45% by mass or less, more preferably about 40% by mass or less, and still more preferably about 35% by mass or less, since having such a solids content achieves excellent production efficiency due to the good fluidity of the liquid during production, and reduces the load on manufacturing equipment due to the low viscosity.

The amount of aripiprazole contained in the suspension is preferably about 0.1 g or more, more preferably about 0.15 g or more, and still more preferably about 0.2 g or more, from the viewpoint of the dose that is necessary to maintain the effective blood concentration required in the treatment after administration into the body. Furthermore, the amount of aripiprazole contained in the suspension is preferably about 0.6 g or less, more preferably about 0.55 g or less, and still more preferably about 0.5 g or less from the viewpoint of safety with respect to the physical stimulus to the body when administered at one time.

The cake composition can be prepared by freeze-drying the suspension. The conditions for freeze-drying may be suitably selected. For example, freeze-drying can be performed by freezing the suspension at −50 to −30° C., followed by drying for 12 hours under reduced pressure of preferably about 5 to 40 Pa and more preferably about 5 to 20 Pa at a temperature of preferably about −15 to 10° C. and more preferably about −10 to 5° C.

The cake composition obtained by freeze-drying the suspension does not break even if external physical impacts are applied thereto, and is capable of maintaining its form as a mass.

The strength of the cake composition is preferably about 5 N or more, more preferably about 10 N or more, and still more preferably about 20 N or more from the following viewpoint. That is, the cake composition does not break during production, transport, or the like due to vibration from the outside, etc.; the cake composition can be easily removed from the container used for freeze drying, which is separate from the storage container; etc. Furthermore, the strength of the cake composition is preferably about 100 N or less, more preferably about 80 N or less, and still more preferably about 50 N or less, from the viewpoint, for example, that the cake composition can be quickly suspended by a dispersion medium when used.

The strength of the cake composition can be measured using an apparatus for measuring stress, such as an Autograph AG-I Universal Testing Instruments (Shimazu Corporation). The strength of the cake composition is measured, for example, by pinching and pressing the cake composition in the vertical direction (i.e., from the top and bottom) and measuring the stress applied until it breaks.

When the cake composition is stored in a container whose inner wall is treated with silicone, in order to reduce the contact with the silicone, it is necessary to prevent the generation of fine particles due to impacts applied during transport, etc. Taking this into consideration, the amount of fine particles formed by the breaking of the cake composition is preferably about 100 mg or less, more preferably about 30 mg or less, and still more preferably about 10 mg or less. Also from the viewpoint of appearance, it is preferable that the generation of fine particles be reduced. The weight of generated fine particles is preferably about 25% or less, more preferably about 10% or less, and still more preferably about 3% or less relative to the total weight of the cake composition.

The breaking of the cake composition is evaluated in the following manner. The cake composition is placed on a sieve with a diameter of 80 mm and openings of 2 mm, and covered with a lid at a location 22 mm above the sieve, and the sieve holding the cake composition is secured in a Bioshaker V-BR-36 produced by TAITEC Co., Ltd. After shaking at 300 rpm for 10 minutes, the weight of the powder that has passed through the sieve is measured.

The cake composition of the present invention may be resuspended by adding the dispersion medium used to prepare the suspension that was used before the freeze-drying. Examples of the dispersion media used for this purpose include water (preferably, distilled water), a polymer aqueous solution, and a surfactant aqueous solution. The resulting resuspended solution is used as an injection liquid.

The amount of the dispersion medium used for resuspending the cake composition is not particularly limited as long as it can be administered subcutaneously or intramuscularly. The amount thereof is preferably 0.5 to 3 mL, and more preferably 1 to 2 mL.

The series of processes for obtaining a medical device containing the cake composition of the present invention is preferably conducted in a sterilized room.

The medical device containing the cake composition of the present invention has a space between the cake composition and the storage container whose inner wall is treated with silicone. This prevents the cake composition from directly contacting the silicone. Accordingly, it is possible to suppress agglomeration of aripiprazole caused by the silicone applied to the inner wall of the storage container when the freeze-dried cake composition is resuspended after long-term storage.

The cake composition of the present invention that comprises aripiprazole as an active ingredient has a specific strength that prevents the cake composition from breaking when external physical impacts are applied and allows the cake composition to be quickly resuspended when mixed with a dispersion medium at the time of use. Therefore, the cake composition of the present invention is suitably used as a cake composition enclosed in a medical device.

Advantageous Effects of Invention

The medical device containing the cake composition of the present invention has a space between the cake composition and the silicone-treated inner wall of the storage container. This reduces the frequency that the cake composition will contact the silicone, and lowers the risk that silicone will contaminate the suspension when the cake composition is resuspended. This allows the aripiprazole, which is an active ingredient contained in the suspension after the resuspension, to be satisfactorily redispersed without agglomerating.

Furthermore, because the cake composition of the present invention containing aripiprazole as an active ingredient has a specific strength, it will not break even when external physical impacts are applied during production and transportation. Moreover, the cake composition can be quickly dispersed without agglomerating when resuspended in a dispersion medium at the time of use.

BRIEF DESCRIPTION OF DRAWINGS

FIG. 1 is a sectional view illustrating one embodiment of a dual chamber syringe.

FIG. 2 is a sectional view showing the dual chamber syringe at the time of use.

FIG. 3 is a sectional view showing the dual chamber syringe at the time of use.

FIG. 4 is a sectional view showing the dual chamber syringe at the time of use.

FIG. 5 is a schematic diagram illustrating a cylindrical cake composition having a sloped side surface.

FIG. 6 is a schematic diagram illustrating a cylindrical cake composition having a sloped side surface and raised top surface.

FIG. 7 is a schematic diagram illustrating one embodiment of the shape of a container, which is separate from the storage container, used for preparing the cylindrical cake composition.

FIG. 8 is a schematic diagram illustrating one embodiment of the shape of a container, which is separate from the storage container, used for preparing the cake cylindrical composition.

FIG. 9 is a sectional view of the schematic diagram illustrating one embodiment of the shape of a container, which is separate from the storage container, used for preparing the cylindrical cake composition.

FIG. 10 is a photograph of the side surface of the cake composition prepared in Example 1.

FIG. 11 is a photograph of the side surface of the cake composition prepared in Example 6.

DESCRIPTION OF EMBODIMENTS

Examples

The present invention is described below in more detail with reference to Examples and Comparative Examples. It should be understood, however, that the present invention is not limited to the following embodiments.

Example 1

The components shown below were individually dissolved or suspended in water to prepare a dispersion containing the components in the following amounts per 1 mL of the final dispersion: 12.48 mg of carboxymethyl cellulose, 62.4 mg of mannitol, 1.11 mg of sodium dihydrogen phosphate monohydrate, and 312.0 mg of aripiprazole hydrate. The pH was adjusted to about 7 with sodium hydroxide.

This suspension was preliminarily pulverized with a high-shear rotary homogenizer (Clearmix, produced by M Technique Co., Ltd.), and then repeatedly wet pulverized with a high-pressure homogenizer (produced by Niro) at 550 bar to a mean particle size of 3 μm or less to thereby produce a suspension of about 30% aripiprazole.

About 1.7 mL of the suspension prepared above (containing about 510 mg of aripiprazole) was inserted into a polyethylene-molded plastic container having an inner side surface sloped at an angle of 2° and having a bottom surface with a thickness of 1 mm or less, the container being deformable so as to allow ejection of a freeze-dried product therefrom when the bottom surface is pressed from the outside. The container containing the suspension was transferred to a freeze-dryer, and freeze-dried according to the cycle described below to obtain a cake composition. The theoretical content of aripiprazole in the cake composition was about 77% by mass. The obtained cake composition had an apparent volume that was substantially the same as the volume originally inserted, with only a slight increase being observed. Thus, the apparent volume was about 1,700 mm$^3$. FIG. 10 shows a photograph of the cake composition.
(a) Thermal treatment: The product was frozen by being maintained at about −40° C. for at least 3 hours.
(b) Primary drying: Primary drying was continued for at least 24 hours at an increased shelf temperature of about −5° C. under a pressure of about 20 Pa or less.

The obtained cake composition was removed from the plastic container. The cake composition had a shape such that the top surface was raised by 2 mm from the inserted liquid level, and the side surface was sloped at an angle of 1° or more. Other cake compositions prepared simultaneously were also measured. The results showed that all of the cake compositions were raised by 0.5 mm or more.

The strength of the obtained cake composition was measured using an Autograph AG-I Universal Testing Instruments (Shimadzu Corporation) by sandwiching and pressing the cake composition of FIG. 6 from the top and bottom. The cake composition had a strength of 49 N.
Results and Discussion The cake composition obtained in Example 1 had a relatively high strength of 49 N. Therefore, the freeze-dried cake composition was easily removed from the container without being broken when ejected from the container.

The cake composition obtained in Example 1 was characterized by slight swelling when freeze-dried. In Example 1, the inner side surface of the plastic container was sloped. Therefore, by using a container that could be deformed by pressing the bottom surface, the freeze-dried cake composition was easily removed from the container without the necessity of using other movable parts for ejecting the cake composition from the container or applying a release agent to the inner surface of the container, while retaining its freeze-dried shape from within the container.

Examples 2-1 to 2-9

1. Production of Siliconized Syringe

Dow Corning®365, 35% Dimethicone NF Emulsion (produced by Dow Corning Corporation) was diluted to various concentrations with purified water. The silicone oil emulsion thus prepared was applied to a glass syringe (inner diameter Φ14.0×length 106 mm; inner area 4,660 mm$^2$, capacity 16,309 mm$^3$), and the water was evaporated to dryness at about 300° C.

The silicone oil applied to the inner surface of the glass was quantified by washing the inner surface of the glass tube with methyl isobutyl ketone, and then measuring the solution using an atomic absorption spectrometer with an Si measurement lamp under the following conditions.
Measurement wavelength: 251.6 nm
Drying: From 50 to 80° C., 40 sec
Ashing: 1,000° C., 20 sec
Atomization: 2,700° C., 5 sec
Cleaning: 2,800° C., 15 sec
Cooling: 17 sec 2. Resuspension of the Cake Composition A suspension containing about 30% aripiprazole with a mean particle size of 2.1 μm was prepared and freeze-dried in the same manner as in Example 1 to obtain a cake composition.

The cake composition was transferred from the plastic container to a siliconized syringe produced as described above in 1. A stopper was disposed within the syringe. To maintain airtightness during storage, the stopper was characterized by being slightly larger than the inner diameter of the syringe and being slidable due to silicone oil applied to the inner side surface of the syringe. The cake composition was transferred into the syringe, and then stored at room temperature for about 1 month. The amount of silicone oil in the cake composition was determined by extracting a resuspension of the cake composition in water with methyl isobutyl ketone, and then measuring the methyl isobutyl ketone solution using an atomic absorption spectrometer.

After storage for about 1 month, the cake composition was resuspended in about 2 mL of water, and the particle size in the suspension was measured using a laser diffraction particle size analyzer produced by Shimadzu Corporation (SALD-3000J or SALD-3100). The measurement was done at a refractive index of 2.00 to 0.20i, using water as the measurement medium in a circulation cell. Separately, the suspension was sonicated for 1 minute with an ultrasonic wave generator attached to the particle size analyzer, and the mean particle size of the sonicated suspension was measured in the same manner as described above.

Table 1 shows the mean particle size of aripiprazole before freeze-drying, the concentration of silicone oil applied to the syringe, the amount of silicone oil on the syringe, the amount of silicone oil after 1-month storage of the syringe containing the cake composition at room temperature and resuspension of the cake composition, and the mean particle size of aripiprazole after resuspension.

TABLE 1

| | | | | One-month storage at room temperature | | |
| --- | --- | --- | --- | --- | --- | --- |
| | Mean particle size of aripiprazole in | Concentration of silicone oil | Amount of silicone oil | Amount of silicone oil in the cake composition after | Mean particle size of aripiprazole (μm) | |
| Example No. | the suspension before freeze-drying (μm) | in the emulsion (% by mass) | on the syringe (μg/100 mm²) | resuspension (μg/100 mg of the active ingredient) | Without Ultrasonic treatment | With ultrasonic treatment |
| 2-1 | 2.1 | 35 | 75 | 22 | 2.1 | 2.1 |
| 2-2 | | 20 | 45 | 6 | 2.1 | 2.1 |
| 2-3 | | 15 | 36 | 7 | 2.1 | 2.0 |
| 2-4 | | 10 | 24 | 4 | 2.1 | 2.0 |
| 2-5 | | 7 | 14 | 4 | 2.1 | 2.1 |
| 2-6 | | 5 | 11 | 3 | 2.1 | 2.0 |
| 2-7 | | 2 | 3 | 5 | 2.0 | 2.0 |
| 2-8 | | 1 | 2 | 4 | 2.0 | 2.0 |
| 2-9 | | 0.5 | 1 | 5 | 2.1 | 2.1 |
| Reference Example | | 0 | 0 | 2 | 2.0 | 2.1 |

Results and Discussion

As shown in Table 1, the amount of silicone oil in the resuspended cake compositions varied according to the concentration of silicone oil in the emulsion applied.

In addition, even when the concentration of silicone oil in the emulsion applied was 0%, silicone oil was detected in the cake composition (Reference Example). This was probably because the silicone oil originally contained in the stopper had transferred to the cake composition. However, because the cake composition had a convex, i.e., raised, top surface as described in Example 1, which minimized the contact of the cake composition with the stopper, the amount of silicone oil mixed into the cake composition was extremely small.

No change in the mean particle size of aripiprazole was observed in any of the syringes prepared using various concentrations of the silicone oil emulsions in Examples 2-1 to 2-9. Agglomeration of particles due to silicone oil can be confirmed by a reduction of the particle size in the measurement under ultrasonic irradiation. The particle size was measured before and after ultrasonic irradiation, and no change was observed in the particle size therebetween. Accordingly, it was determined that no agglomeration had occurred.

Example 3

A suspension containing about 30 mass % aripiprazole was prepared in the same manner as in Example 1, and freeze-dried to obtain a cake composition.

A dual chamber syringe with an inner diameter of 14 mm as shown in FIG. 1 (capacity of the chamber in which the cake composition was enclosed: about 3,000 mm³) was used as the syringe, and a middle stopper 4 as shown in FIG. 1 was fitted using the sleeve cap method. After about 1.7 mL of water was inserted into the syringe, an end stopper 5 was fitted using the sleeve cap method.

The aripiprazole-containing cake composition obtained by freeze-drying in a plastic container was removed from the plastic container by pressing the bottom surface of the plastic container, and directly transferred to a space on a middle stopper 4 as shown in FIG. 1 in the syringe in which water was inserted. A front stopper 3 as shown in FIG. 1 was fitted using the sleeve cap method. A front assembly 12 as shown in FIG. 1 was fitted onto the syringe to obtain a prefilled syringe containing the cake composition with aripiprazole as an active ingredient.

The apparent volume of the cake composition was about 60% of the capacity of the storage container of the prefilled syringe (the capacity of the chamber in which the cake composition was enclosed). The end stopper was pressed by a plunger to allow water as a redispersion medium to flow into the chamber A in which the cake composition was enclosed. After mixing, the syringe was vigorously shaken to achieve complete resuspension. The end stopper was pressed to the end to expel the medicinal fluid from the syringe. The amount of medicinal fluid remaining in the syringe was measured and found to be about 36 to 40 mg (about 38 mg on average).

This is the amount of medicinal fluid remaining in the gaps of the stopper and the front assembly, i.e., the so-called dead space of the outlet. It was considered that the prefilled syringe obtained by this method fully performed the functions required for administration.

Likewise, using a prefilled syringe in which the cake composition containing aripiprazole as an active ingredient was enclosed, the end stopper was slowly pressed to allow water as a redispersion medium to flow into a front chamber for about 5 seconds. Without shaking the syringe at all, the end stopper was pressed to the end to expel the suspension from the syringe.

The amount of medicinal fluid remaining in the syringe was measured and found to be about 74 to 95 mg (about 85 mg on average). The amount of medicinal fluid remaining in the gaps of the stopper and the front assembly, i.e., the so-called dead space of the outlet, was about 38 mg on average. Since the syringe was not shaken, about 47 mg, which was obtained by subtracting 38 mg from 85 mg, remained in the syringe. However, it was considered that the prefilled syringe obtained by this method was satisfactorily to perform the functions required for administration.

Example 4

The components shown below were individually dissolved or suspended in water to prepare a dispersion containing the components in the following amounts per 1 mL of the final dispersion: 8.32 mg of carboxymethyl cellulose, 4.16 mg of mannitol, 0.74 mg of sodium dihydrogen phosphate monohydrate, and 208.0 mg of aripiprazole hydrate. The pH was adjusted to about 7 with sodium hydroxide.

This suspension was preliminarily pulverized with a high-shear rotary homogenizer (Clearmix, produced by M Technique Co., Ltd.), and then repeatedly wet pulverized with a high-pressure homogenizer (produced by Niro) at 550 bar to a mean particle size of 3 μm or less to thereby produce a suspension containing about 20 mass % aripiprazole.

About 2 mL of the suspension prepared above (containing about 400 mg of aripiprazole) was inserted into a polyethylene-molded plastic container having an inner side surface sloped at an angle of 2° and having a bottom surface with a thickness of 1 mm or less, the container being deformable so as to allow ejection of a freeze-dried product therefrom when the bottom surface was pressed from the outside. The container containing the suspension was transferred to a freeze-dryer, and freeze-dried according to the cycle described below to obtain a cake composition. The theoretical content of aripiprazole in the cake composition was about 77% by mass. The obtained cake composition had an apparent volume that was substantially the same as the volume originally inserted, with only a slight increase being observed. Thus, the apparent volume was about 2,000 mm$^3$.
(a) Thermal treatment: The product was frozen by being maintained at about −40° C. for at least 3 hours.
(b) Primary drying: Primary drying was continued for at least 24 hours at an increased shelf temperature of about −5° C. under a pressure of about 20 Pa or less.

The obtained cake composition was removed from the plastic container by pressing the bottom surface of the plastic container. The cake composition was easily removed from the container while retaining its freeze-dried shape from within the container, without the necessity of using other movable parts for ejecting the cake composition from the container or applying a release agent to the inner surface of the container.

Examples 5-1 to 5-3

A suspension containing about 30 mass % aripiprazole was prepared in the same manner as in Example 1. This suspension was diluted with purified water to suspensions containing about 10 mass, 20 mass %, and 30 mass % aripiprazole. These suspensions were freeze-dried in the same manner as in Example 1 to obtain cake compositions. Table 2 shows the ease of removal of the obtained cake compositions from the containers.

TABLE 2

| Example No. | Concentration of aripiprazole (% by mass) | Strength (N) | Removal from the container |
|---|---|---|---|
| 5-1 | 10.5 | 6.90 | Smoothly removed from the container. |
| 5-2 | 20.8 | 42.29 | Smoothly removed from the container. |
| 5-3 | 32.5 | 48.98 | Smoothly removed from the container. |

Results and Discussion

Each of the aripiprazole-containing cake compositions obtained by freeze-drying in a plastic container was removed from the plastic container by pressing the bottom surface of the plastic container. All of the cake compositions obtained in Examples 5-1 to 5-3 were easily removed from the containers. The strength of the cake compositions obtained by freeze-drying was measured using an Autograph AG-I Universal Testing Instruments (Shimadzu Corporation) in the same manner as in Example 1. The cake composition produced by using the suspension containing about 10 mass % aripiprazole prepared in Example 5-1 had a strength of about 7 N. Even when the container is configured to allow easy removal, the cake composition must have some strength.

Example 6

A container as described in Example 1 was produced using polypropylene, and a cake composition was produced in the same manner as in Example 1.

The cake composition obtained by freeze-drying in the plastic container was removed from the plastic container by pressing the bottom surface of the plastic container, and directly transferred to a syringe. The cake composition was easily removed from the container while retaining its freeze-dried shape from within the container, without the necessity of using other movable parts for ejecting the cake composition from the container or applying a release agent to the inner surface of the container. FIG. 11 shows a photograph of the cake composition obtained.

It was confirmed that the obtained cake composition had an elevated portion on the circumference of the upper surface. The obtained cake composition was raised by 0.5 mm or more on the circumference of the upper surface, although the shape was different from that of the cake composition obtained using the polyethylene container described above in Example 1.

The cake composition was enclosed in a syringe to produce a prefilled syringe (capacity of the chamber in which the cake composition was enclosed: about 3,500 mm$^3$). The apparent volume of the cake composition was about 50% of the capacity of the storage container of the prefilled syringe (the capacity of the chamber in which the cake composition was enclosed). The syringe used was a so-called single chamber type having only one space for containing a medicinal agent. The freeze-dried cake composition was easily resuspended by drawing water as a redispersion medium into the syringe during the resuspension.

Example 7

A suspension containing about 30 mass % aripiprazole was obtained in the same manner as in Example 1. About 1.5 mL to about 1.7 mL of this suspension was inserted into a polyethylene-molded plastic container, and freeze-dried to obtain a cake composition. The obtained cake composition weighed about 600 mg. This cake composition was placed on a sieve with 2 mm openings and a diameter of 80 mm, and covered with a lid that was 22 mm above the sieve. The sieve was secured in a Bioshaker V-BR-36 produced by TAITEC Co., Ltd., and shaken at 300 rpm for 10 minutes. The amount of powder passing through the sieve openings was about 1 to 9 mg.

Results and Discussion

The results of Example 7 showed that in spite of being produced by freeze-drying, this cake composition was not brittle and was less likely to break and generate fine powder due to impacts during transportation, etc. Freeze-dried cake compositions are generally brittle, and often break due to strong impacts as in the above test. If fine powder is generated from this pharmaceutical preparation, it may come into contact with the silicone on the inner surface A in FIG. 1 and thereby increase the particle size, etc.; furthermore, the generation of fine powder would cause an undesirable appearance. The above results showed that this production method can produce a cake composition whose surface is not brittle and from which it is unlikely to generate fine powder.

Examples 8-1 to 8-3

A suspension containing about 30% aripiprazole was obtained in the same manner as in Example 1 except that sucrose was used in place of mannitol. The suspension was diluted with purified water in the same manner as in Example 5 to suspensions containing about 10 mass, 20 mass, and 30 mass % aripiprazole. Using plastic containers, the suspensions were freeze-dried. As in Example 1, without the necessity of using other movable parts for ejecting the cake composition from the container or applying a release agent to the inner surface of the container, each cake composition was easily removed from the container while retaining its freeze-dried shape from within the container. Table 3 shows the ease of removal of the obtained cake compositions from the containers.

TABLE 3

| Example No. | Concentration of aripiprazole (% by mass) | Strength (N) | Removal from the container |
|---|---|---|---|
| 8-1 | 11.2 | 11.01 | Smoothly removed from the container |
| 8-2 | 21.4 | 33.04 | Smoothly removed from the container. |
| 8-3 | 32.8 | 48.72 | Smoothly removed from the container. |

Results and Discussion

Even when mannitol was used in place of sucrose, the cake composition produced using a suspension containing about 10 mass % aripiprazole had a strength of about 11 N.

Comparative Examples 1-1 to 1-9

A suspension containing about 30 mass % aripiprazole with a mean particle size of 2.2 μm was prepared in the same manner as in Example 1. Into syringes produced by applying silicone oil emulsions of various concentrations prepared in Example 2 and drying, a middle stopper with an outer diameter slightly larger than the inner diameter of the syringe was fitted using the sleeve cap method. About 1.5 mL of the suspension was inserted into the space on the middle stopper, and freeze-dried as is within the syringe. After the freeze-drying, a front stopper was fitted using the sleeve cap method.

After freeze-drying, the syringes were stored at room temperature for about 1 month, and the amount of silicone oil in the cake composition was measured in the same manner as in Example 2. In each of the syringes containing the cake composition, the cake composition adhered to the syringe tube, and there was no space between the inner wall of the syringe and the cake composition.

Table 4 shows the mean particle size of aripiprazole before freeze-drying, the concentration of silicone oil applied to the syringe, the amount of silicone oil on the syringe, the amount of silicone oil after 1-month storage of the syringe containing the cake composition at room temperature and resuspension of the cake composition, and the mean particle size of aripiprazole after resuspension.

TABLE 4

| | | | | One-month storage at room temperature | | |
|---|---|---|---|---|---|---|
| Comparative Example No. | Mean particle size of aripiprazole in the suspension before freeze-drying (μm) | Concentration of silicone oil in the emulsion (% by mass) | Amount of silicone oil on the syringe (μg/100 mm²) | Amount of silicone oil in the cake composition after resuspension (μg/100 mg of the active ingredient) | Mean particle size of aripiprazole (μm) | |
| | | | | | Without ultrasonic treatment | With ultrasonic treatment |
| 1-1 | 2.2 | 35 | 75 | 49 | 3.5 | 2.5 |
| 1-2 | | 20 | 45 | 41 | 3.1 | 2.3 |
| 1-3 | | 15 | 36 | 49 | 3.1 | 2.4 |
| 1-4 | | 10 | 24 | 38 | 3.1 | 2.4 |
| 1-5 | | 7 | 14 | 27 | 2.9 | 2.4 |
| 1-6 | | 5 | 11 | 24 | 2.8 | 2.3 |
| 1-7 | | 2 | 3 | 26 | 2.7 | 2.2 |
| 1-8 | | 1 | 2 | 16 | 2.6 | 2.3 |
| 1-9 | | 0.5 | 1 | 19 | 2.5 | 2.3 |
| Reference Example | | 0 | 0 | 14 | 2.3 | 2.2 |

Results and Discussion

The results shown in Table 4 indicate that the higher the concentration of silicone oil emulsion applied to the syringe, the higher the silicone oil content of the cake composition; and the higher the concentration of silicone oil applied to the syringe, the greater the change in the mean particle size. Compared to a prefilled syringe preparation using the cake composition obtained by freeze-drying in a storage container different from that described in Example 2, different results were obtained even at the same concentration of silicone oil emulsion applied.

Even when the concentration of silicone oil in the emulsion applied was 0%, silicone oil was detected in the cake composition. This was probably because the silicone oil originally contained in the stopper had transferred to the cake composition.

When agglomerated particles are measured under ultrasonic irradiation, the size of loose particles changes. When the particle size was measured under ultrasonic irradiation in this Comparative Example, a reduction in particle size was observed. This result indicates that according to the method comprising freeze-drying in a syringe, silicone oil causes agglomeration.

Comparative Examples 2-1 to 2-12

Suspensions containing about 20 mass % aripiprazole with a mean particle size of 2.0 μm and 2.4 μm were individually prepared in the same manner as in Example 4. Into syringes produced by applying the silicone oil emulsions of various concentrations prepared in Example 2, a middle stopper with an outer diameter slightly larger than the inner diameter of the syringe was fitted using the sleeve cap method. About 2 mL of the suspension was inserted into the space on the middle stopper, and freeze-dried as is within the syringe. In each of the syringes containing the cake composition, the cake composition adhered to the syringe tube, and there was no space between the inner wall of the syringe and the cake composition.

After the freeze-drying, the syringes were stored at room temperature for 1 month, 2 months and 3 months. After the storage, the cake composition within the syringes was resuspended in about 2 mL of water, and the mean particle size was measured in the same manner as in Example 2. Table 5 shows the concentration of silicone oil applied to the syringe, the mean particle size of aripiprazole before freeze-drying, and the mean particle size of aripiprazole after storage at room temperature for 1 month, 2 months, and 3 months, and resuspension.

TABLE 5

| Comparative Example No. | Concentration of silicone oil in the emulsion (% by mass) | Mean particle size of aripiprazole in the suspension before freeze-drying (μm) | Mean particle size (measurement without ultrasonic treatment) (μm) | | |
|---|---|---|---|---|---|
| | | | One-month storage at room temperature | Two-month storage at room temperature | Three-month storage at room temperature |
| 2-1 | 35 | 2.0 | 3.7 | 3.6 | 5.3 |
| 2-2 | 30 | | 3.3 | 3.8 | 3.6 |
| 2-3 | 25 | | 2.6 | 2.9 | 3.1 |
| 2-4 | 20 | | 3.3 | 3.4 | 4.5 |
| 2-5 | 15 | | 2.6 | 3.0 | 2.6 |
| 2-6 | 10 | 2.4 | 3.3 | 3.6 | 3.5 |
| 2-7 | 7 | | 3.1 | 3.1 | 3.1 |
| 2-8 | 5 | | 2.9 | 2.9 | 2.9 |
| 2-9 | 2 | | 2.6 | 2.7 | 2.7 |
| 2-10 | 1 | | 2.5 | 2.7 | 2.6 |
| 2-11 | 0.5 | | 2.5 | 2.6 | 2.5 |
| 2-12 | 0.2 | | 2.5 | 2.6 | 2.6 |

Results and Discussion

As shown in Table 5, the results indicate that the higher the concentration of silicone oil emulsion applied to the syringe, the greater the change in the particle size. As in Comparative Example 1, even with the use of a suspension containing about 20 mass % aripiprazole, if the cake composition obtained by freeze-drying within a syringe was resuspended as is, changes in the mean particle size of aripiprazole were observed.

Comparative Example 3

A suspension containing about 30 mass % aripiprazole was prepared in the same manner as in Example 1. Into a syringe produced by applying a 5 mass % silicone oil emulsion in the same manner as in Example 2, a middle stopper with an outer diameter slightly larger than the inner diameter of the syringe was fitted using the sleeve cap method. About 1.5 mL of the suspension was inserted into the space on the middle stopper, and the syringe was transferred to a freeze-dryer. The suspension was freeze-dried according to the cycle described below to prepare a syringe in which the cake composition was enclosed. In the syringe containing the cake composition, the cake composition adhered to the syringe tube, and there was no space between the inner wall of the syringe and the cake composition.
(a) Thermal treatment: The product was frozen by being maintained at about −40° C. for about 3 hours.
(b) Primary drying: Primary drying was continued for at least 24 hours at an increased shelf temperature of about −5° C. under a pressure of about 20 Pa or less.

A front stopper was fitted above the cake composition within the obtained syringe (on the needle side, at the position of front stopper 3 shown in FIG. 1) using the sleeve cap method. About 1.7 mL of water as a redispersion medium was inserted into chamber B, which is defined by the middle stopper and the end stopper of the prefilled syringe. The end stopper was fitted using the sleeve cap method. A front assembly was incorporated into the syringe tip ejection portion. The end stopper was slowly pressed to allow water as a redispersion medium to flow into a front chamber for about 5 seconds. Without shaking the syringe at all, the end stopper was pressed to the end to expel the medicinal fluid from the syringe. The amount of medicinal fluid remaining in the syringe was measured and found to be about 159 mg.

Results and Discussion

A dual chamber prefilled syringe preparation is generally prepared by being freeze-dried within a syringe as described in Comparative Example 3. Similar to the above, after water was allowed to flow into a front chamber over a period of about 5 seconds, a medicinal fluid was expelled without shaking the syringe at all. The amount of medicinal fluid remaining was measured and found to be about 159 mg, i.e., a very large amount. Thus, the results show that compared to the method of Example 3, in which about 85 mg of medicinal fluid remained, the general method described in Comparative Example 3 exhibited poor redispersibility.

REFERENCE SIGNS LIST

A: Chamber
B: Chamber
1: Dual chamber syringe
2: Syringe tube
3: Front stopper
4: Middle stopper
5: End stopper
6: Tip
7: Opening
8: Cake composition
9: Injection liquid
10: Silicone
11: Bypass
12: Front assembly
13: Hypodermic needle
14: Plunger
15: Suspension
a: Angle
a': Angle
L: Length from the raised top point to the top surface
16: Container
17: Opening
18: Bottom surface
19: Outer frame

The invention claimed is:

1. A medical device containing a separately prepared freeze-dried cake composition comprising aripiprazole as an active ingredient in a storage container whose inner wall is treated with silicone,
    wherein the medical device is a dual-chamber syringe,
    the dual-chamber syringe has a front stopper and a middle stopper,
    there is a space between the inner wall of the storage container and the cake composition,
    the cake composition has a cylindrical shape,
    a side surface of the cylindrical cake composition is sloped,
    an angle of the slope is 0.1 to 10 degrees,
    a top surface of the cylindrical cake composition is raised,
    a distance between the peak of the raised portion and the top surface is 0.5 to 5 mm, and
    the cake composition is enclosed such that contact with the front stopper or the middle stopper is reduced due to the raised portion of the top surface.

2. The medical device containing the cake composition according to claim 1, wherein the cake composition is a cake composition that was freeze-dried in a container separate from the storage container.

3. The medical device containing the cake composition according to claim 1 or 2, wherein the apparent volume of the cake composition accounts for 30 to 99% of the volume of the storage container.

4. The medical device containing the cake composition according to claim 1 or 2, wherein the storage container treated with silicone is a vial or syringe.

5. The medical device containing the cake composition according to claim 4, wherein the syringe has multiple chambers and the cake composition is contained in at least one chamber.

6. The medical device containing the cake composition according to claim 4, wherein the syringe has a chamber (A) for containing the cake composition, and a chamber (B) for containing an injection liquid;
    the chamber (A) is arranged on the side where a needle is placed, and the chamber (B) is arranged on the side where a plunger is placed; and
    the cake composition is contained in the chamber (A) and the injection liquid is contained in the chamber (B).

7. The medical device containing the cake composition according to claim 1 or 2, wherein the cake composition has a strength of 5 to 100 N.

* * * * *